US012558212B2

(12) United States Patent
Williams et al.

(10) Patent No.: US 12,558,212 B2
(45) Date of Patent: Feb. 24, 2026

(54) FIXATION DEVICE AND METHOD OF MANUFACTURE AND USE

(71) Applicant: INNOVATE ORTHOPAEDICS LIMITED, Huddersfield (GB)

(72) Inventors: Andrew Michael Williams, London (GB); Alexander John Gutteridge, Huddersfield (GB)

(73) Assignee: INNOVATE ORTHOPAEDICS LIMITED, Slaithwaite (GB)

( * ) Notice: Subject to any disclaimer, the term of this patent is extended or adjusted under 35 U.S.C. 154(b) by 1247 days.

(21) Appl. No.: 17/184,260

(22) Filed: Feb. 24, 2021

(65) Prior Publication Data

US 2021/0177569 A1      Jun. 17, 2021

Related U.S. Application Data

(63) Continuation of application No. 16/068,582, filed as application No. PCT/GB2016/054081 on Dec. 28, 2016, now Pat. No. 10,959,830.

(30) Foreign Application Priority Data

Jan. 7, 2016      (GB) ...................................... 1600263

(51) Int. Cl.
*A61F 2/08*      (2006.01)
*A61B 17/68*      (2006.01)
(Continued)

(52) U.S. Cl.
CPC ........ *A61F 2/0811* (2013.01); *A61B 17/8645* (2013.01); *A61B 2017/681* (2013.01);
(Continued)

(58) Field of Classification Search
CPC .............. A61B 17/863; A61B 17/8645; A61B 2017/00783; A61B 17/864;
(Continued)

(56) References Cited

U.S. PATENT DOCUMENTS 5,730,744 A      3/1998  Justin et al.
5,871,486 A *    2/1999  Huebner .............. A61B 17/863
                                                          606/305
(Continued)

FOREIGN PATENT DOCUMENTS

CN      202960741      6/2013
CN      103648422      3/2014
(Continued)

OTHER PUBLICATIONS

"2.0mm Cannulation RCI Screws," Smith & Nephew India, 2 pages [retrieved online from: www.smith-nephew.com/india/products/endoscopy/knee/rci].
(Continued)

*Primary Examiner* — Christopher D. Prone
(74) *Attorney, Agent, or Firm* — Sheridan Ross P.C.

(57)      ABSTRACT

A method and apparatus are disclosed for providing a compression fixation between a first and further component. The apparatus comprises an elongate body having a head end and a tip end and comprising a screw thread including a first region in which the screw thread has a corresponding first pitch and a further region, extending from the tip end, in which the screw thread is tapered and has a corresponding farther pitch that continually decreases away from the tip end.

13 Claims, 8 Drawing Sheets

(51) Int. Cl.
  *A61B 17/86* (2006.01)
  *A61B 17/88* (2006.01)
(52) U.S. Cl.
  CPC ........... *A61B 17/863* (2013.01); *A61B 17/864*
  (2013.01); *A61B 17/8897* (2013.01); *A61F*
  *2002/0841* (2013.01); *A61F 2002/0858*
  (2013.01); *A61F 2002/0894* (2013.01)
(58) Field of Classification Search
  CPC ........... A61B 17/8897; A61B 2017/681; A61F
  2/0811; A61F 2002/0858; A61F
  2/2427–2439; A61F 2002/0841; A61F
  2002/0894
  See application file for complete search history.

(56) References Cited

U.S. PATENT DOCUMENTS

| | | | |
|---|---|---|---|
| 5,964,768 | A | 10/1999 | Huebner |
| 6,156,037 | A | 12/2000 | LeHuec et al. |
| 6,283,973 | B1 * | 9/2001 | Hubbard ............... A61F 2/0811 |
| | | | 606/104 |
| 6,468,277 | B1 | 10/2002 | Justen et al. |
| 6,863,671 | B1 | 3/2005 | Strobel et al. |
| D565,181 | S | 3/2008 | Anitua |
| D577,122 | S | 9/2008 | Aldecoa |
| D601,253 | S | 9/2009 | Kahdemann |
| D622,847 | S | 8/2010 | Berberich |
| D628,292 | S | 11/2010 | Berberich |
| 9,808,298 | B2 | 11/2017 | Stroncek et al. |
| 10,959,830 | B2 | 3/2021 | Williams et al. |
| 2006/0100627 | A1 | 5/2006 | Stone et al. |
| 2006/0173462 | A1 | 8/2006 | Kay et al. |
| 2006/0217727 | A1 | 9/2006 | Munro et al. |
| 2007/0038221 | A1 | 2/2007 | Fine et al. |
| 2007/0162029 | A1 | 7/2007 | Whitmore |
| 2008/0161864 | A1 | 7/2008 | Beck et al. |
| 2008/0243192 | A1 | 10/2008 | Jacene et al. |
| 2008/0249579 | A1 | 10/2008 | Taylor |
| 2009/0198288 | A1 * | 8/2009 | Hoof .................... A61F 2/0811 |
| | | | 606/301 |
| 2010/0042167 | A1 | 2/2010 | Nebosky et al. |
| 2010/0217329 | A1 | 8/2010 | Brown et al. |
| 2010/0298888 | A1 | 11/2010 | Graf et al. |
| 2011/0270326 | A1 | 11/2011 | Black et al. |
| 2012/0022603 | A1 | 1/2012 | Kirschman |
| 2012/0158137 | A1 | 6/2012 | Pinczewski |
| 2012/0296428 | A1 | 11/2012 | Donner |
| 2013/0211468 | A1 | 8/2013 | Huebner |
| 2013/0245685 | A1 | 9/2013 | Contiliano et al. |
| 2014/0052177 | A1 | 2/2014 | Singhatat et al. |
| 2014/0194937 | A1 * | 7/2014 | Asnis ................... A61F 2/0811 |
| | | | 606/316 |
| 2014/0200620 | A1 | 7/2014 | Yahov |
| 2014/0277190 | A1 | 9/2014 | Splieth et al. |
| 2017/0303912 | A1 | 10/2017 | Elattrache et al. |

FOREIGN PATENT DOCUMENTS

| | | |
|---|---|---|
| WO | WO 92/03980 | 3/1992 |
| WO | WO 95/15727 | 6/1995 |
| WO | WO 2015/052195 | 4/2015 |

OTHER PUBLICATIONS

Arthrex, Metal Interference Screws, 8 pages [retrieved online from: www.arthrex.com/knee/metal-interference-screws/products?types= all&locales=en&taxonomy=soft_screws&time=0&sort=relevan].
DePuy Synthes. Profile TM and Advantage TM Interference Screws, last updated Feb. 4, 2019, 2 pages [retrieved online from: www. depuysynthes.com/hcp/mitek-sports-medicine/products/qs/PROFILE-and-ADVANTAGE-Interference-Screws].
Coleridge et al. "A comparison of five tibial-fixation systems in hamstring-graft anterior cruciate ligament reconstruction," Knee Surg Sports Traumatol Arthrose., 2004, vol. 12, pp. 391-397.
Crosnier et al. "A novel method to assess primary stability of press-fit acetabular cups," Journal of Engineering in Medicine, 22014, vol. 228, No. 11, pp. 1126-1134.
Donahue et al. "Comparison of Viscoelastic, Structural, and Material Properties of Double-Looped Anterior Cruciate Ligament Grafts Made From Bovine Digital Extensor and Human Hamstring Tendons," Transactions of the ASME, Apr. 2001, vol. 123, pp. 162-169.
Halewood et al. "The fixation strength of a novel ACL soft-tissue graft fixation device compared with conventional interference screws: a biomechanical study in vitro," Knee Surg Sports Traumatol Arthrose, 2011, vol. 19, pp. 559-567.
International Search Report and Written Opinion issued by the European Patent Office, dated Mar. 24, 2017, for International Application No. PCT/GB2016/054081; 14 pages.

* cited by examiner

FIXATION DEVICE AND METHOD OF MANUFACTURE AND USE

CROSS-REFERENCE TO RELATED APPLICATIONS

This application is a continuation of U.S. patent application Ser. No. 16/068,582, filed Jul. 6, 2018, now issued as U.S. Pat. No. 10,959,830, which is a U.S. National Stage under 35 U.S.C. § 371 of International Patent Application No. PCT/GB2016/054081 filed Dec. 28, 2016, which claims the benefit of Patent Application No. GB1600263.6 filed Jan. 7, 2016, each of which is incorporated herein by reference in its entirety.

BACKGROUND

The present invention relates to apparatus and a method for providing a compression fixation between various components. In particular, but not exclusively, the present invention relates to a fixation device such as an interference screw having an elongate body which includes a screw thread that has a varying pitch at a tip end and a constant pitch along another region of the body. The varying pitch enables easy and accurate starting of the screw in use whilst the constant pitch region of the screw thread provides good fixation.

Various methods and fixation devices are known for fixing various components with respect to each other in the medical field. For example methods and apparatus are known for attaching tissue and/or bone into bone for the purpose of ligament reconstructions and/or repair. An example is a fixation device. Some conventional fixation devices have commonly been referred to as interference screws. Some interference screws are cannulated. In conventional techniques cannulation of a fixation device allows a device to be positioned and inserted into bone over a guide wire which increases accuracy and reduces divergence. Commonly the interference screw is inserted using an orthopaedic screwdriver.

A purpose of a fixation device is to provide compression fixation, commonly known as an interference fit, between two components in order to hold those components in place with respect to each other. This can, for example, be used to hold ligaments in place that connect two bones across a joint. It is known that the majority of use of such devices tends to be in respect of the knee joint of humans or other animals. Conventionally interference screws have been used in the tibia, femur or fibula or a combination of these and can be used with a combination of components of either soft tissue graft or bone blocks attached to soft tissue grafts.

Grafts may take the form of allograft tissue (deceased donor sourced replacement ligaments), autograft (a replacement ligament sourced from the same individual body), artificial replacement ligaments and/or augmentation of ligaments in situ or the like. Depending upon the form these grafts take bone may need to be fixed to bone, ligament fixed to bone or artificial manmade fibres or fibre fixed to bone.

It is common practice when providing such compression fixation that a tunnel is drilled in a bone and a graft of a selected type may be inserted into the tunnel and held in place with a fixation device. The fixation device, such as an interference screw, is commonly placed alongside the graft at the interface between the graft and bone or bone and bone in order to compress the parts of the graft and/or bone together and thereby provide compression fixation. It is also known that such fixation devices can be inserted into the middle of a graft if using four hamstring grafts, for example, in order to provide 360° graft-to-bone contact. Conventionally the fixation device is placed in a linear not perpendicular fashion with respect to a pre-prepared tunnel and pre-located graft.

US2006/0100627 illustrates an interference screw which can be used as a fixation device for securing tissue to a bone.

Whilst many conventional interference screws and other fixation devices work well in practice there are a number of key problems associated with their use. For example during a surgical operation a surgeon must attempt to locate the fixation device at a desired location and at a desired orientation so that as the fixation device is driven into bone and/or tissue the interference screw does not cause undue damage to soft tissue present at the fixation site. This may compromise fixation. Likewise surgeons carrying out operations with conventional screws must exert considerable urging force to begin a screwing process. As some surgeons may carry out multiple operations on any single day this can result in tiredness and exhaustion of the human surgeons carrying out the operations and this can lead to errors.

SUMMARY

It is an aim of the present invention to at least partly mitigate the above-mentioned problems.

It is an aim of certain embodiments of the present invention to enable apparatus that can be used for providing a compression fixation to be accurately located at a desired orientation to minimise likelihood of tissue damage during an initial phase of a screwing operation.

It is an aim of certain embodiments of the present invention to provide an apparatus for providing a compression fixation which is easier and quicker to start screwing into opposed matter than is available with conventional fixation devices.

It is an aim of certain embodiments of the present invention to provide a method and apparatus for providing a compression fixation between a first and further component such as a bone or graft or bone and bone or graft and graft.

It is an aim of certain embodiments of the present invention to help reduce an axial urging and/or rotating force necessary to engage a screw thread and insert a screw.

It is an aim of certain embodiments of the present invention to provide an interference screw which will need fewer turns to achieve a predetermined linear penetration before a main region of a screw thread used primarily to provide compression fixation becomes engaged.

It is an aim of certain embodiments of the present invention to allow a fixation device to be inserted and reliably located so as to minimise initial disruption and/or damage to a replacement graft or other such component.

According to a first aspect of the present invention there is provided apparatus for providing a compression fixation between a first and further component, comprising an elongate body having a head end and a tip end and comprising a screw thread including a first region in which the screw thread has a corresponding first pitch and a further region, extending from the tip end, in which the screw thread is tapered and has a corresponding further pitch that continually decreases away from the tip end.

Aptly the further pitch continuously decreases from the tip end to the first region of the screw thread.

Aptly the first region of the screw thread blends into the further region of the screw thread at a location of the elongate body where the first region of the screw thread begins to taper inwards towards the tip end.

Aptly a distance between adjacent turns of the screw thread along the elongate body constantly decreases from the tip end to a location where the distance between adjacent turns becomes constant.

Aptly the screw thread in the first region has a constant pitch between adjacent turns.

Aptly the constant pitch of the screw thread in the first region is about around 0.5 to 3.5 mm.

Aptly the constant pitch is about around 2.0 to 2.5 mm.

Aptly the constant pitch is between 2.0 and 2.5 mm.

Aptly the further region of the screw thread has a varying pitch that varies by decreasing continuously and constantly away from the tip end.

Aptly the screw thread in the further region extends more than one revolution around the elongate body.

Aptly the crest of the screw thread in the first and further regions has a common radius.

Aptly the first region of screw thread comprises a straight thread and the further region of screw thread comprises a tapered thread that blends into the straight thread.

Aptly the elongate body comprises a central through passage extending from the tip end to the head end.

Aptly the through passage comprises a cannulation.

Aptly the elongate body comprises a head portion that extends from the head end to a cylindrical threaded portion, that provides said first region of the screw thread, and that comprises a substantially cylindrical body including a driver element at the head end, for receiving a mating end of a driver member, and a thread origin where an outer surface of the cylindrical body is recessed to form a start of the first region of the screw thread and the cylindrical threaded portion.

Aptly the driver element comprises a hex-shaped recess in the head portion for receiving a working end of an orthopaedic screwdriver.

Aptly the head portion includes at least one visible indicia element having a position associated with a location of a start site of the further region of the screw thread at the tip end of the elongate body.

Aptly the elongate body is integrally formed.

Aptly an overall length of the elongate body is about around 20 to 40 mm.

Aptly the overall length of the elongate body is about around 25 to 35 mm.

Aptly an overall outer diameter of the elongate body is about around 5 to 15 mm.

Aptly the overall outer diameter is about around 6 to 12 mm.

Aptly the elongate body is a fixation device and is manufactured from titanium, PEEK or PLLA or the like.

Aptly the first component comprises a bone region and the further component comprises one or more of a further bone region or a ligament or at least one artificial fibre.

According to a second aspect of the present invention there is provided a method of providing a compression fixation between a bone and at least one further component, comprising the steps of:

screwing an elongate body comprising a head end, a tip end and a screw thread into a pre-prepared tunnel in a bone; and as the elongate body is screwed into the tunnel, advancing the elongate body at an advancement rate that continually reduces from an initial start rate until a constant rate of advancement is reached, said constant rate being slower than the start rate.

Aptly the advancement rate indicates a linear distance travelled by the elongate body per revolution as the elongate body is rotated.

Aptly the method comprises providing a continuous reduction in advancement rate via a region of a screw thread of the elongate body that has a pitch that continuously decreases away from the tip end.

Aptly the step of screwing comprises simultaneously rotating the elongate body and urging the elongate body in a desired direction along the tunnel.

According to a third aspect of the present invention there is provided use of a fixation device having an initially reducing and then constant lead for the fixation of a bone to at least one of a further bone or ligament or artificial fibre.

According to a fourth aspect of the present invention there is provided apparatus constructed and arranged substantially as herein before described with reference to the accompanying drawings.

According to a fifth aspect of the present invention there is provided a method substantially as herein described with reference to the accompanying drawings.

Certain embodiments of the present invention provide an apparatus and method for providing a compression fixation between a first and at least one further component which is easier to use and less prone to causing damage than is possible with conventional techniques and devices.

Certain embodiments of the present invention provide an apparatus and method for providing a compression fixation in which an elongate body having a screw thread can initially be screwed at a high rate of advancement. That is to say initially an elongate body travels a relatively large linear distance per revolution of the body which helps make an easy/quick start during a screwing process.

According to certain embodiments of the present invention a fixation device has a screw thread which has a varying pitch whereby the pitch at the tip of the elongate body continually decreases away from a tip end to provide an immediate relatively large distance of travel per rotation followed by a gradual reduction in such a rate of advancement up until a main region of the thread is engaged which then provides a constant rate of advancement and high degree of compression and thus fixation.

Certain embodiments of the present invention provide one or more visible indicators at an end or other part of an elongate body used as a fixation device away from a penetrating tip region. The indicator or indicators has/have a predetermined relationship with a start site of a thread at a tip of the elongate body so that by locating the indicia at a predetermined rotatory orientation a surgeon or other care giver knows where a start point of a screwing process will begin. This helps avoid undue damage during an initial phase of a compression fixation operation.

BRIEF DESCRIPTION OF THE DRAWINGS

Embodiments of the present invention will now be described hereinafter, by way of example only, with reference to the accompanying drawings in which.

In the drawings like reference numerals refer to like parts.

DETAILED DESCRIPTION

Figure 1:
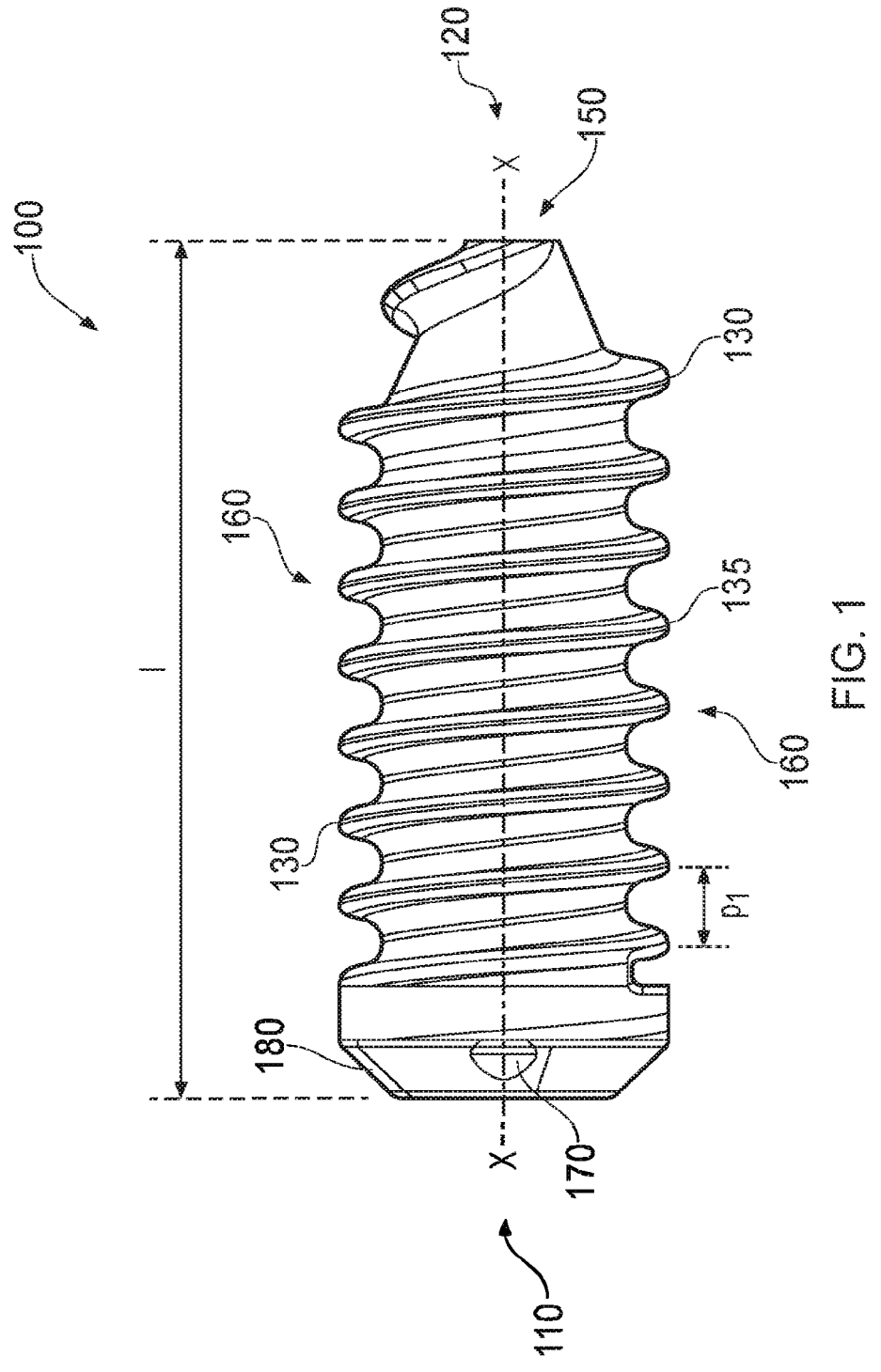
FIG. 1 illustrates apparatus for providing a compression fixation.

FIG. 1 illustrates a view of apparatus for providing a compression fixation between a first and further component. FIG. 1 illustrates an example of a fixation device in the form of an interference screw 100. It will be appreciated that certain embodiments of the present invention are not restricted to such fixation devices. As illustrated in FIG. 1 the interference screw 100 is formed as an elongate body having a head end 110 and a tip end 120. The elongate body shown is integrally formed. It will be appreciated that alternatively a multi-part body could be assembled and parts of the body secured together via conventional techniques. A screw thread 130 extends along a large proportion of the overall length l of the elongate body. The screw thread is a helical structure which can be used to convert rotational force to linear movement. The screw thread 130 shown is a ridge 135 wrapped around and projecting from a substantially cylindrical region of the elongate body and around a substantially cone-shaped region of the elongate body in the form of a helix. The region of the screw thread which is wrapped around a substantially cylindrical portion of the elongate body provides a region of straight thread. The region of the screw thread which is wrapped around a tapered portion of the elongate body leading to the tip end provides a tapered thread. It will be appreciated that other shapes of underlying supporting structure provided by the body in regions between the ridged thread could be utilised. Also a slight taper may be present on the substantially cylindrical region of the screw thread. Aptly the substantially cylindrical region has a taper of up to 5°. Aptly the cylindrical region has a common outer diameter along its length.

The screw thread 130 of the elongate body has a variable lead. That is to say a pitch, or distance between ridges of adjacent windings of the screw thread, varies from the tip end 120 of the screw 100 towards the head end 110. At the tip end the thread has a pitch which provides a lead whereby a linear distance travelled by the screw per revolution is relatively high relative to the lead or linear distance travelled by the screw in one revolution provided by the screw thread in the central, substantially cylindrical region of the screw thread.

It will be appreciated that a helix of a thread can twist in one of two possible directions which is often referred to as handedness. Certain embodiments of the present invention include threads orientated with a right handed or left handed screw thread. In the elongate body shown in FIG. 1 the screw thread is shown as a right handed screw thread.

Lead is associated with the distance along a screws axis that is covered by one complete rotation of the screw. Pitch is the distance from the crest of one thread to the crest on an adjacent thread. It will be appreciated that the elongate body of the interference screw 100 shown in FIG. 1 includes a single start screw thread which means that there is effectively only one ridge wrapped around the underlying body of the screw. Whilst reference is made to the thread being 'wrapped' around the elongate body it will be appreciated that the thread is not necessarily a separate element literally wound/wrapped around an underlying part of the screw. Optionally this is of course possible. Aptly the elongate body including the thread is integrally formed.

FIG. 1 helps illustrate how the pitch pi in the region of the screw thread where the screw thread is cylindrical (that is to say has a constant outer diameter) is constant between adjacent windings. By contrast at the tip end 120 of the elongate body the screw thread makes a different and varying pitch angle with respect to the longitudinal axis X of the screw. The tapered portion of the outer surface of the elongate body at the tip end thus includes a screw thread which is tapered and has a pitch which continually decreases away from the tip end. That is to say at the tip end where a start point 150 of the screw thread begins the thread provides a predetermined immediate advancement rate. That is to say the screw thread is such that the elongate body will advance by a predetermined linear distance per revolution on start up. The pitch continually decreases away from the tip end. That is to say the pitch continually decreases towards the head end 110 of the elongate body until the thread blends into the thread of the screw thread in the substantially cylindrical region of the screw. It will be appreciated that an intermediate region of screw thread between the substantially cylindrical region and the tapered region could optionally be included. Aptly the further pitch of the screw thread near the tapered end continuously decreases from the tip end to the first region of the screw thread where the screw thread has a substantially cylindrical outer diameter. Aptly the first region of the screw thread blends into the further region of the screw thread at a location of the elongate body where the first region of the screw thread begins to taper inwards towards the tip end. The screw thread does not taper inwards completely to a single point but rather has a slightly truncated or snub nose. This is illustrated in more detail in the following Figures and is because of the fact that the screw is cannulated to be used with a guide wire. Non cannulated fixation devices according to certain other embodiments of the present invention can of course taper to a point.

Aptly the constant pitch of the screw thread in the first region of the screw where the screw thread is substantially cylindrical is about around 0.5 to 3.5 mm. Aptly the constant pitch is about around 2.0 to 2.5 mm. Aptly the constant pitch is between 2.0 and 2.5 mm. As illustrated in FIG. 1 the screw thread in the further region of the elongate body near the tip extends by more than 1 revolution around the elongate body. That is to say there is more than one revolution of the screw thread during which the pitch of the thread continuously decreases away from the tip end. Alternatively of course less than one revolution of the thread is possible in the tapered region of the screw thread near the tip end. Aptly the screw thread in the further region of the elongate body near the tip extends by more than 1.5 revolutions.

As illustrated in FIG. 1 the crest 160 of the screw thread shown is constant along a whole length of the screw thread. Aptly the crest has a common radius from its beginning at the head end region of the elongate body to the tip end. Alternatively the crest may have a variable shape along the length of the thread. Aptly, as an alternative, the crest is thinner nearer the tip end.

FIG. 1 also helps illustrate how a notch 170 in a bevelled surface 180 at the head end 110 of the screw can be used to provide a visible indicator aligned with the start point 150 of the screw thread at the tip end 120 of the screw. It will be appreciated that one, two, three or more elements can be utilised to provide a visible indicator. Each visible indicator is an element or combination of elements which are visible to a surgeon or other healthcare giver and which can be used as a rotary alignment guide. Whilst the screw 100 shown in FIG. 1 includes a single notch it will be appreciated that notches, recesses, projections, bosses, grooves, coloured lines or other alignment indicating elements could be utilised according to certain other embodiments of the present invention. Likewise these can be positioned in other locations on the fixation device than on the head as is shown in FIG. 1. What is important is that there is at least one indicium which is visible or at least detectable in some way and is known to have a predetermined orientational relationship with a location on the elongate body where a screw thread start point begins. Thus a surgeon can orientate the screw around its elongate axis by rotating and simultaneously viewing the visible cue and will know with certainty that a start of a screwing process will begin at a particular desired location. Having the indicator at the head end 110 of the screw is particularly useful when a surgeon is likely to be able to most easily view an end portion of the screw. It will be appreciate that according to certain other embodiments of the present invention the indicia/indicium may be located at any other region of the screw.

Figure 2:
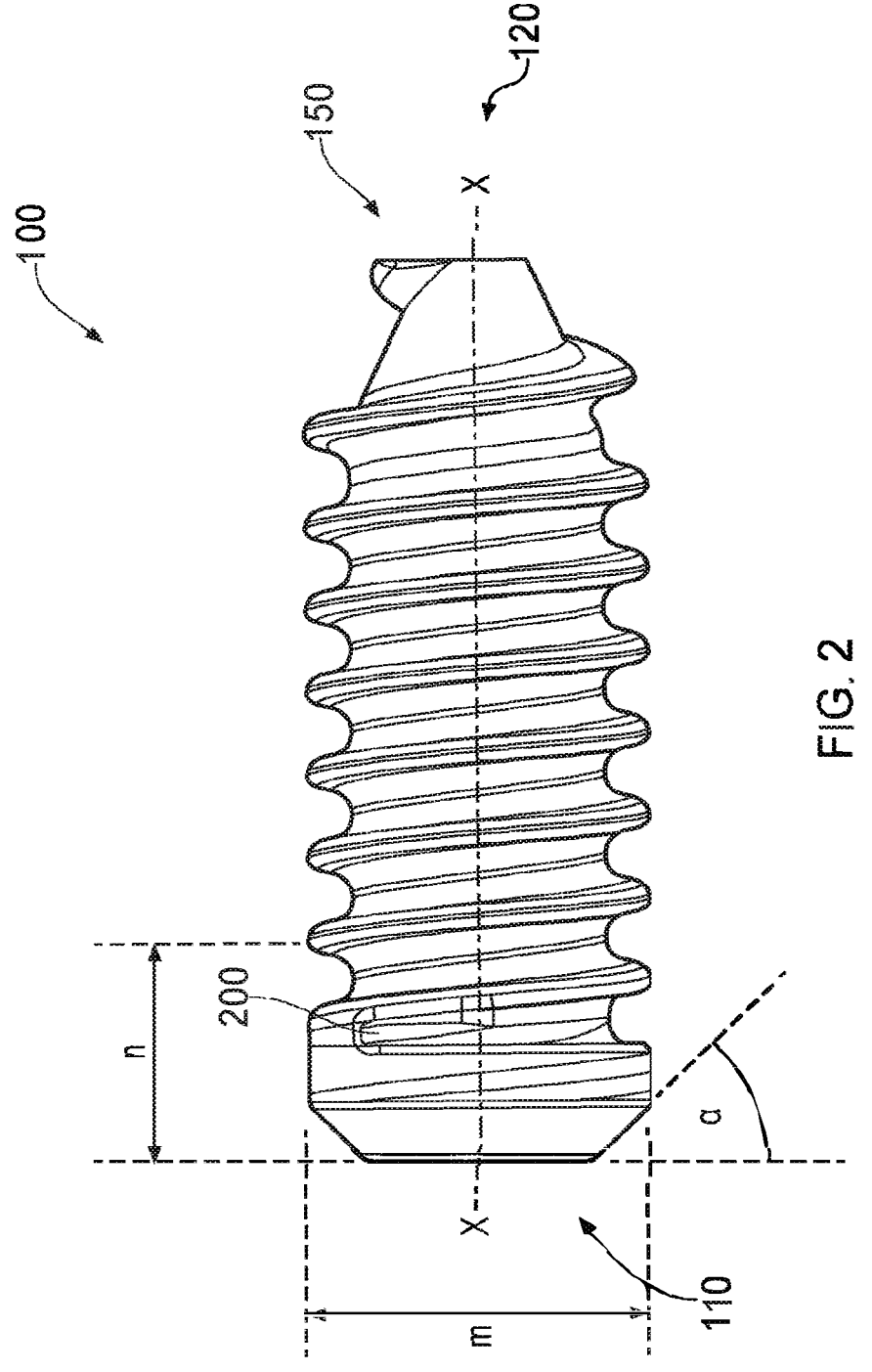
FIG. 2 illustrates another view of the apparatus for providing a compression fixation shown in FIG. 1.

FIG. 2 help illustrate a reverse side view of the fixation device 100 illustrated in FIG. 1. FIG. 2 helps illustrate the start point 150 of the screw thread at the tip end 120 of the elongate body. FIG. 2 also help illustrate the tapered outer surface of the interference screw at the tip end and how the screw thread in this tapered region itself tapers. That is to say an outer diameter defined by the crest of the thread narrows towards the tip end 120. FIG. 2 also helps illustrate the region of the screw thread which has a common outer diameter m which corresponds to (or alternatively is greater than) the outer diameter at the head end 110 of the interference screw. As discussed previously with respect to FIG. 1 the head end is bevelled having an angle α which in the example shown in FIG. 2 is 45°. Aptly the bevel is between about around 40° and 50°. The head end of the interference screw thus has a frusto conical outer surface at the head end where the head is bevelled which then leads into a substantially cylindrical portion before the beginning point 200 of the screw thread.

Figure 3:
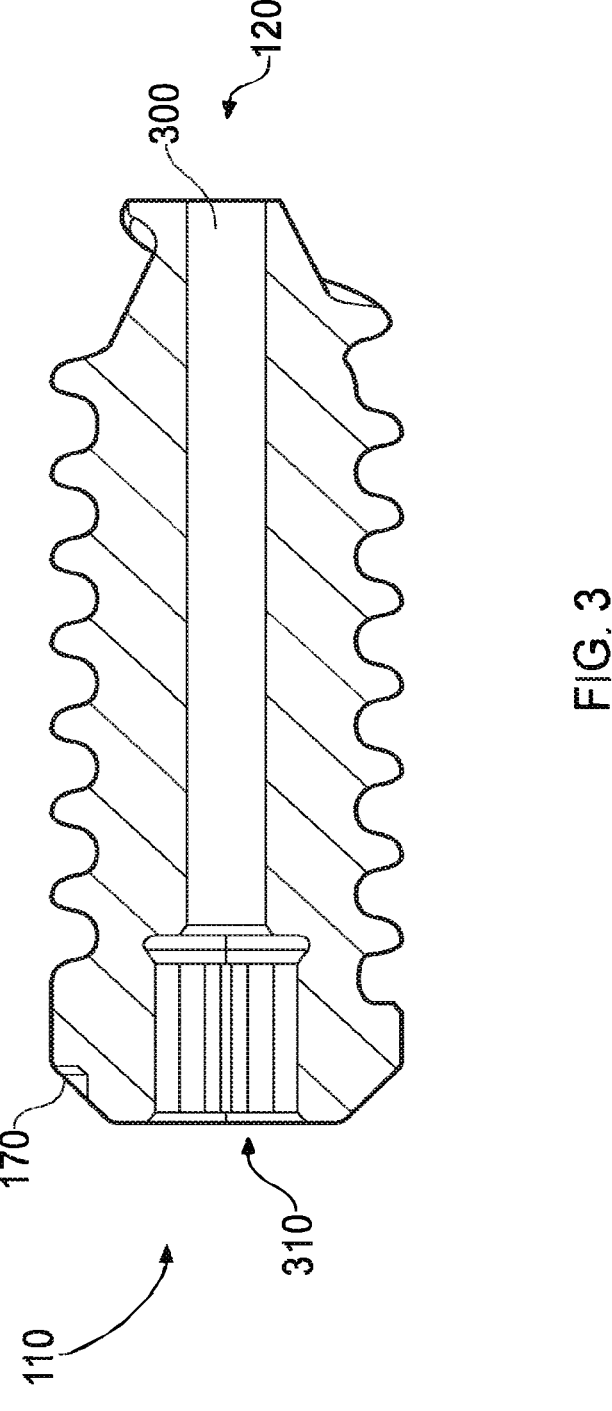
FIG. 3 illustrates a cut-through view of apparatus for providing a compression fixation.

FIG. 3 is a cut through view of the interference screw 100 shown in FIGS. 1 and 2. FIG. 3 helps illustrate how a longitudinal passage 300 extends through the centre of the body of the interference screw. The through bore provided by the passage 300 is used to enable the interference screw to be used with a guide wire which is an element commonly used in certain surgical operations. The longitudinal bore 300 has a common diameter extending along much of the elongate body from the tip of the interference screw towards the head end 110, The longitudinal bore opens into a wider open mouth 310 which is used to receive a driver element such as an orthopaedic screw driver or the like to enable the interference screw to be urged in a direction from the head end to the tip end and turned in use. The bore is aligned with the central longitudinal axis of the screw.

FIG. 3 also helps illustrate the position of a single alignment indicator 170. The indicator 170 is an alignment mark which has a predetermined location arrangement with respect to the start of the screw thread. The mark may take a variety of forms such as laser etching or machined mark. The mark may be visible to a surgeon when starting to insert a screw. The mark can line up directly with the start of the thread on the tip of the screw as shown in the figures but may optionally be aligned in a different predetermined relationship which would previously be understood by the surgeon or health care provider making use of the interference screw. It will be appreciated that the indicator or another indicator or indicators can also be used as a guide to line up with a predetermined mark or feature of the driver element (such as an orthopaedic screw driver) used by the surgeon or health care giver. In this way at least one indicator acts as a rotatory alignment guide so that a surgeon can easily orientate a screw driver to a desired combination to immediately start screwing and/or orientate the interference screw so that the screw thread start point can be set against a desired component or region of a component at a surgical site.

Figure 4:
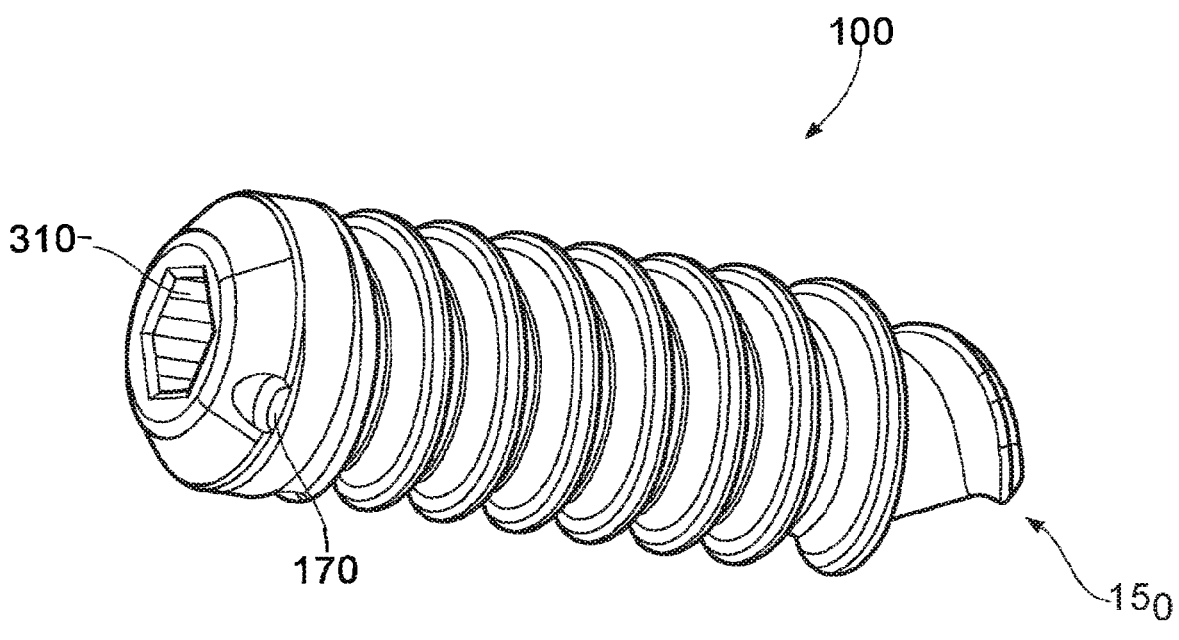
FIG. 4 illustrates another view of apparatus for providing a compression fixation.

FIG. 4 helps illustrate how the gaps between windings of the thread vary along the length of the elongate body from the tip 120 towards the head 110 of the interference screw. More particularly FIG. 4 helps illustrate the main body section from the trailing end to the start of the tapered section of the interference screw. FIG. 4 helps illustrate how the thread has a constant pitch along this main body section of the interference screw and has a tapered leading end. The thread has an increasing pitch from the start of the tapered section right up to the leading end of the screw. A cannulation runs along the length of the interference screw from a driver socket formed as an open mouth of the central bore to the trailing end. It will be appreciated that according to certain other embodiments of the present invention, rather than provide a driver socket as an open mouth 310, a boss having a predetermined cross section or other such projecting element may extend from the head end which would be received in a corresponding and mating female or inset region at an end of a driver element. The main body section of the interference screw with the thread which has a constant pitch helps provide fixation of a graft in a bone tunnel through compression. The tapered leading end and thread which has an increasing pitch towards the tip helps allow the screw to engage in the bone tunnel and start quickly upon rotation of the screw until the main body thread is engaged. The cannulation helps allow the insertion of the screw over a guide wire and the driver socket allows the engagement of a driver element, such as a universally accepted 3.5 hex orthopaedic screwdriver, with the interference screw to permit use.

Certain embodiments of the present invention thus provide a fixation device suitable for interference fixation. Aptly certain embodiments of the present invention are not fracture screws. Aptly the fixation device according to certain embodiments of the present invention is not designed to work with an orthopaedic plate. Aptly the interference screw according to certain embodiments of the present invention has a variable thread on the distal tip region of the screw to aid insertion. Aptly the variable screw thread is not provided on a proximal end region of the interference screw. Aptly certain embodiments of the present invention are provided for interference fixation not bone compression.

Figure 5:
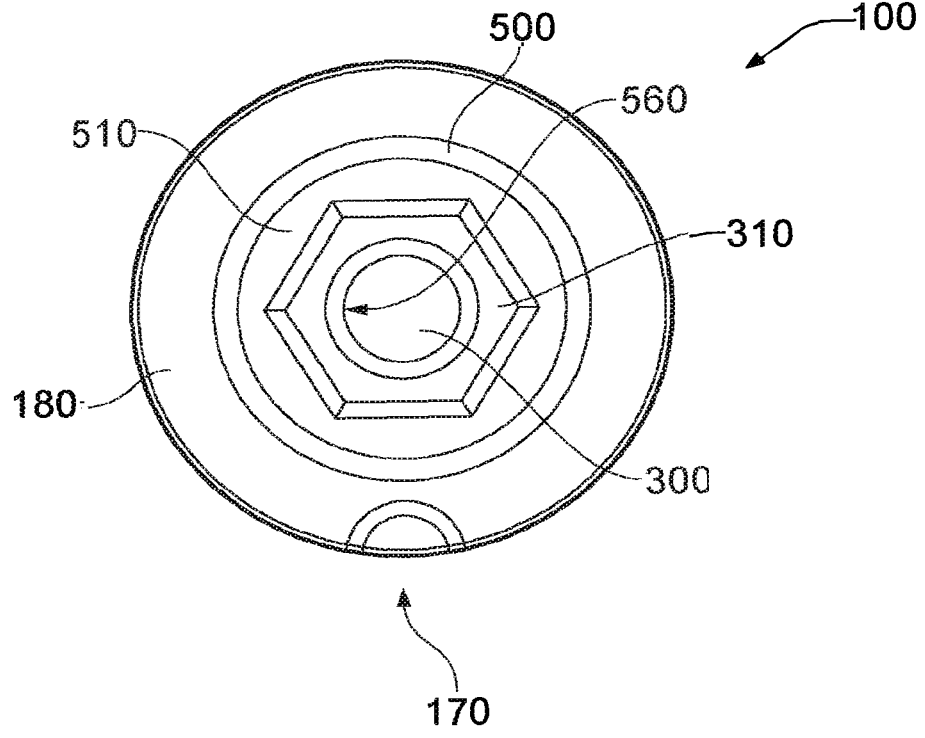
FIG. 5 illustrates a head end of an elongate body usable for providing a compression fixation.

FIG. 5 helps illustrate an end view from the head end 110 of the fixation device 100. The outer diameter of the interference screw has an outer diameter of between 5 and 15 mm. Aptly the outer diameter is 9 mm. The outer diameter provides an outer circular extent of the interference screw. The bevelled surface 160 is illustrated in FIG. 5 leading from the outer diameter inwardly and the single notch 170 which acts as an indicator is shown formed in that bevelled surface. The bevelled surface is curved to provide a rounded region 500 at the head end and this then leads into a flat end surface 510. This flat surface then curves inwardly into a hexagonal-shaped open mouth 310. The central through bore 300 which is provided by a substantially cylindrical smooth inner surface through the screw is illustrated in FIG. 5 in the centre of the interference screw. A bottom of the hex shaped mouth is flat before a rounded edge leads into the central bore that has a circular inner surface 560.

Figure 6:
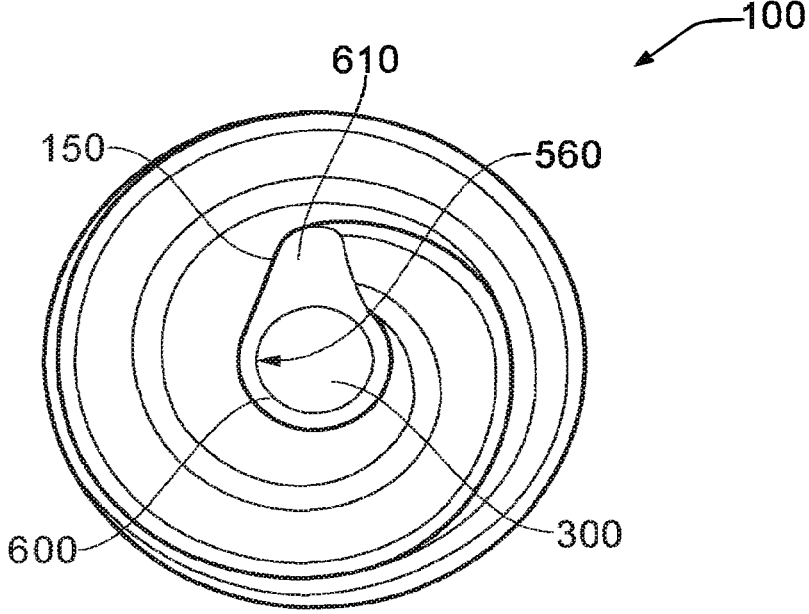
FIG. 6 illustrates a tip end of an elongate body for providing a compression fixation.

FIG. 6 helps illustrate an end view of the tip end of the interference screw and helps illustrate how the through bore 300 extends all the way through along the longitudinal axis of the interference screw. A small annular surface 600 provides the actual end point of the elongate body. Aptly the thickness of this end surface is about around 0.15 to 0.5 mm. Aptly the thickness is 0.3 mm. The annular surface 600 also includes a small extension 610 where the start point 150 of the screw thread begins on the tapered surface of the screw. FIG. 6 helps illustrate how at the tapered end of the interference screw the screw thread winds outwards having a constantly increasing outer diameter provided by the crest of a screw thread. After about around 1.5 to 2 revolutions of the screw thread the screw thread outer diameter (provided by the apex of the ridge) has reached the maximum outer diameter of the screw thread where the screw thread then adopts a common outer diameter as the screw thread blends into the region of the elongate body which has a constant pitch and constant outer diameter.

Figure 7B:
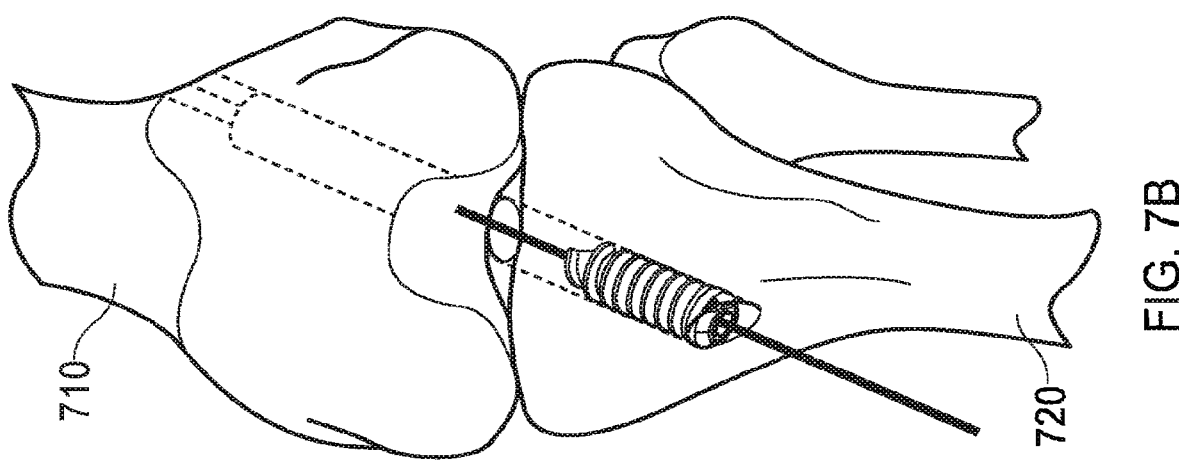
FIG. 7A and FIG. 7B illustrate a screwing process into a tunnel formed in a bone.
Figure 7A:
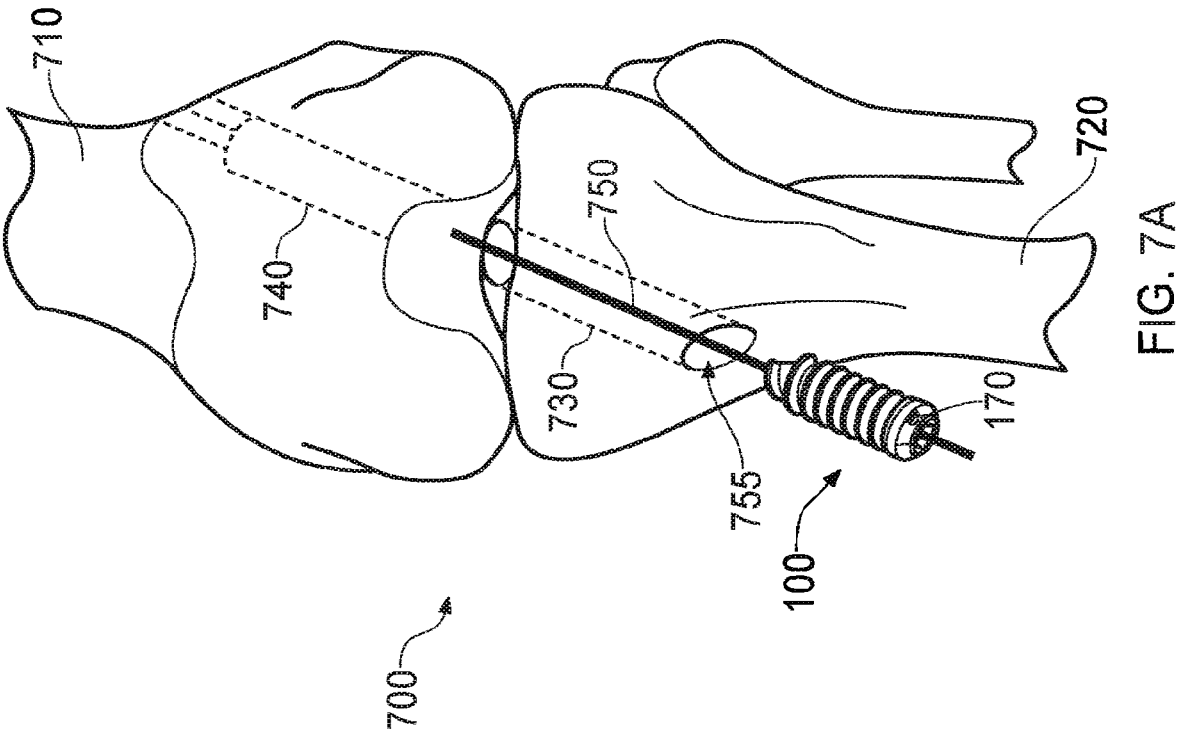

FIG. 7A and FIG. 7B illustrate the general anatomy before and after screw insertion when the fixation device 100 is used as part of arthroscopic knee surgery. It will be appreciated that certain embodiments of the present invention are usable in a wide range of surgical operations. FIG. 7A illustrates bones of the knee region 700 before insertion of the interference screw 100. FIG. 7A illustrates a femur 710 and tibia 720. A tibial tunnel 730 is formed in the tibia 720 and a femoral tunnel 740 is pre-prepared in the femur. A guide wire 750 can be inserted along the tibial tunnel 730 and/or femoral tunnel 740. The guide wire guides the fixation device 100. The fixation device 100 can be passed over the guide wire and located at an opening 755 of the tibial tunnel 730 or femoral tunnel 740. A surgeon can move the interference screw easily towards the tunnel and then rotate the screw using the locating notch 170 as a guide to align the corresponding start point of the thread at a desired location.

FIG. 7B helps illustrate how, subsequent to orientation at a desired rotatory position, the interference screw 100 can then be screwed into the tibial tunnel by rotating the screw and simultaneously urging it forwards along the tunnel. The screwing process can be carried out by a wide range of tools such as a driver (not shown) which can include a handle and a suitably shaped shaft for engaging the screw. Aptly the driver is also cannulated so as to be usable with a guide wire. It will be appreciated that the driver includes a driving head that mates with the corresponding driving element (a hex recess for example) of the interference screw.

Figures 8A, 8B:
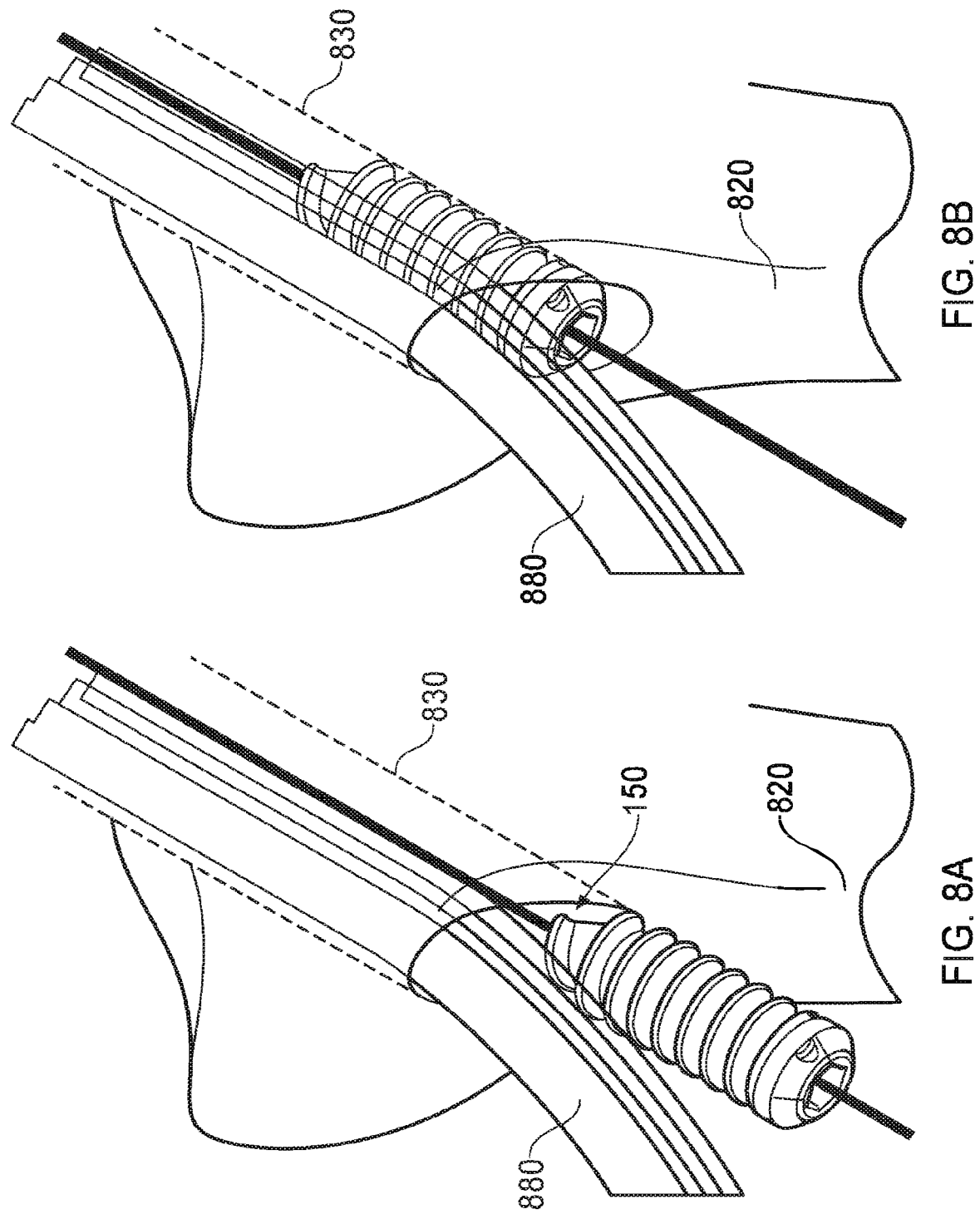
FIGS. 8A and 8B illustrate compression fixation between bone and tissue.

FIGS. 8A and 8B help illustrate how a tibia 820 which includes a tibial tunnel 830 can be provided with a graft 880. The graft illustrated in FIG. 8 is a hamstring graft although it will be appreciated that according to certain other embodiments of the present invention a wide range of tissue/graft component parts can be utilised in a wide range of opening at an end of the tibial tunnel and orientated so that the start point of the thread 150 is orientated so as to begin cutting into the bone of the tibia rather than into the graft 880. Subsequent to an appropriate rotatory orientation a surgeon, using a suitable driver, can then screw the interference screw 100 along the tunnel guided by the guide wire. Immediately the screw finds purchase into the bone and is drawn into the bone advancing along the tunnel at an advancement rate that reduces from the immediate start rate to a constant advancement rate. FIG. 8B helps illustrate the position of the interference screw as it is screwed into the tunnel 830 where it provides a compression fixation to secure the graft with respect to the bone. It will be appreciated that subsequent to the interference screw being screwed into a desired position the guide wire can be subsequently removed and the passage closed by conventional techniques.

EXAMPLES

In an embodiment, the fixation device is an interference screw referred to with the name "Quick-Start".

An insertion study has been carried out by imperial College London, UK. The study was devised to test what advantage in terms of engagement with bone as the screw is started, is provided by certain embodiments of the present invention. Two different types of screws were used in the study. One type of screw was a Quick-Start (QS) screw and the other was a conventional interference screw (IS).

Materials and Methods

A purpose built rig was designed to hold a block of solid rigid polyurethane foam (Sawbones Europe AB, Sweden) of density 0.48 g/cm³ as representative of good quality, high-density cancellous bone. Each block was pre-drilled with two pairs of 8 mm holes as substitute bone tunnels, through which polyester shoelaces were inserted and applied with 20N from hanging weights (this substituted as a soft-tissue graft in the tunnel). A force/torque sensor (Omega 85; ATI Industrial Automation, Apex NC) was mounted behind the polyurethane blocks to record data during the experiment.

Seven consultant surgeons were asked to insert one QS and one IS (9×25 mm) into a pair of tunnels. The order of the QS/IS screw for the pair of tunnels was randomised, and the screw design was blinded from the surgeon by holding a graft sizing tube over the screw, guide wire and screwdriver head. During the insertion of the screws the axial force and torque was recorded from the sensor, and from analysing pilot data the screw was deemed to have first engaged in the tunnel when it exceeded a threshold torque value of 0.2 Nm.

The following data was analysed: the number of attempted turns until the screw engaged (denoted by number of force peaks prior to engaging); the initial torque when the screw engaged; the axial force when the screw engaged; the maximum axial force experienced during the insertion; and the average torque during the first five turns of the screw after engaging (the term 'turn' defined an attempted rotation of the screw made by the surgeon, as denoted by a peak in the torque/axial force data, and did not refer to a full revolution of the screw/screwdriver). Each surgeon attempted 4 pairs of QS/IS screws, and was asked after each pair of QS/IS (whilst still blinded) which screw felt the easiest to initially insert.

Statistical analysis was performed in SPSS 23 (IBM SPSS Statistics, version 23, Armonk, NY). Pairs of data were tested for normality using Shapiro-Wilk tests. The initial insertion torque, initial and peak axial forces were assessed using a paired-sampled t-test; the number of attempted turns before engaging and the average torque from five turns were assessed using the non-parametric Wilcoxon signed-rank test.

Results

Table 1 shows the data from the insertion test. One pair of data was not recorded fully during the test and was thus excluded from the analysis, leaving 27 pairs of data from the seven consultant surgeons.

The IS screw took an average 5 turns before engaging in the tunnel, whereas the QS engaged on average after 2 turns (Wilcoxon signed-rank test, p<0.001). in terms of axial force applied by the surgeon, the initial force required to engage the screw in the tunnel was is larger for the IS than the QS (Paired-samples t-test, p=0.008). This was also found to be the case for the peak axial force required for the IS and the QS (Paired-samples West, p<0.001).

TABLE 1

Data from the insertion test (mean data ± standard deviation)

| n = 27 | IS | QS |
|---|---|---|
| Number of attempted turns before engaging | 5 ± 4** | 2 ± 1 |
| Initial axial force applied when engaged (N) | 104 ± 50* | 83 ± 43 |
| Peak axial force applied (N) | 130 ± 55** | 100 ± 39 |
| Initial insertion torque when engaged (Nm) | 0.2 ± 0.1** | 0.3 ± 0.1 |
| Average torque from first 5 turns when engaged (Nm) | 0.3 ± 0.1** | 0.8 ± 0.3 |
| Which screw felt easiest to initially insert (blinded feedback by the surgeon)? | 3 | 24 |

*indicates a significant difference between the conventional interference screw (IS) and the Quick-Start (QS) screw (p < 0.05).
**indicates when this significance is p < 0.001.

The initial insertion torque when the screw engaged was larger for the QS than the IS (Paired-samples t-test, p<0.001). This was also the case when averaging the first five turns atter the screw has engaged for the QS than the IS (Wilcoxon signed-rank test, p<0.001).

When the surgeons were asked subjective feedback about which screw felt easiest to initially insert into the tunnel (whilst blinded to the choice of screw), 24 out of the 27 pairs were chosen as the QS, which equates to 89% of the pairs.
Discussion The important finding of this study is that the QS screw engaged with the bone tunnel more easily than a conventional IS. For soft-tissue reconstruction, quickly engaging the screw into the bone tunnel and requiring fewer turns reduces the likelihood of graft damage on insertion.

The insertion test supports the view that the QS requires less number of turns to initially engage the screw into the graft tunnel and less axial force applied by the surgeon through the screwdriver than the IS. This data reflects the design of the modified tip, which gives greater purchase and grips the tunnel easily. This is further supported by the subjective feedback from the surgeons that in the 89% of the tests, the QS felt as if it engaged more easily than the IS even when the choice of screw was blinded to them.

Once the screw engaged in the tunnel, the QS screw demonstrated a higher insertion torque than the IS in both the initial torque as well as the average of the first 5 turns. Thus the QS screw grips more quickly with the bone tunnel than the IS. Also more rotational energy may be applied to the graft which is compressed to the sides of the tunnel.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of providing a compression fixation via an interference fit between a bone and at least one further component, comprising:
   screwing an elongate body comprising a head end, a tip end and a screw thread into a pre-prepared tunnel in a bone, wherein:
   the elongate body advances at a predetermined initial advancement rate as the tip end is initially screwed into the tunnel, and
   after initially advancing at the initial advancement rate, the elongate body advances at a continually decreasing advancement rate until the elongate body reaches a constant advancement rate; wherein a continuous reduction in the continually decreasing advancement rate is provided via a distal tip region of the screw thread, that has a pitch that continuously decreases away from the tip end, and that blends into a central substantially cylindrical region of the screw thread that provides the constant advancement rate and that has a constant pitch.

2. The method of claim 1, wherein each of the initial advancement rate, the continually decreasing advancement rate, and the constant advancement rate indicate a linear distance travelled by the elongate body per revolution as the elongate body is rotated.

3. The method of claim 1, wherein screwing the elongate body comprises simultaneously rotating the elongate body and urging the elongate body in a desired direction along the tunnel.

4. The method of claim 1, wherein the pre-prepared tunnel is selected from a tibial tunnel and a femoral tunnel.

5. The method of claim 1, further comprising:
   prior to screwing the elongate body, inserting at least one guide wire along the pre-prepared tunnel in the bone.

6. The method of claim 5, further comprising:
   passing the elongate body over the at least one guide wire via a cannulation in the elongate body.

7. The method of claim 1, further comprising:
   prior to screwing the elongate body, providing at least one graft component in an opening at an end of the pre-prepared tunnel.

8. The method of claim 1, further comprising:
   prior to screwing the elongate body, using a locating notch as a guide to align a corresponding start point of the screw thread at a desired location.

9. The method of claim 8 wherein the start point of the thread is orientated so as to begin cutting into the bone rather than into a graft.

10. The method of claim 1, wherein advancing the elongate body provides a compression fixation to secure a graft with respect to the bone.

11. The method of claim 1, wherein the at least one further component comprises at least one of a further bone or ligament or artificial fibre.

12. The method of claim 1, wherein screwing the elongate body is performed by a driver that comprises a handle and a shaft shaped for engaging the elongate body.

13. The method of claim 12, wherein the driver is cannulated so as to be usable with a guide wire.

\* \* \* \* \*